(12) United States Patent
Wong

(10) Patent No.: US 8,222,025 B2
(45) Date of Patent: *Jul. 17, 2012

(54) MULTISTORY BIOREACTION SYSTEM FOR ENHANCING PHOTOSYNTHESIS

(76) Inventor: Lan Wong, Hong Kong (HK)

( * ) Notice: Subject to any disclaimer, the term of this patent is extended or adjusted under 35 U.S.C. 154(b) by 11 days.

This patent is subject to a terminal disclaimer.

(21) Appl. No.: 13/091,146

(22) Filed: Apr. 21, 2011

(65) Prior Publication Data

US 2011/0197317 A1    Aug. 11, 2011

Related U.S. Application Data

(63) Continuation-in-part of application No. 12/729,258, filed on Mar. 23, 2010.

(60) Provisional application No. 61/413,429, filed on Nov. 13, 2010.

(51) Int. Cl.
*C12M 1/00* (2006.01)
(52) U.S. Cl. .................................. 435/292.1
(58) Field of Classification Search ................ 435/292.1
See application file for complete search history.

(56) References Cited

U.S. PATENT DOCUMENTS

| | | | |
|---|---|---|---|
| 4,235,043 A | 11/1980 | Harasawa et al. | |
| 4,333,263 A | 6/1982 | Adey | |
| 4,626,065 A | 12/1986 | Mori | |
| 4,952,443 A | 8/1990 | Gravisse | |
| 5,097,795 A | 3/1992 | Adey | |
| 5,162,051 A | 11/1992 | Hoeksema | |
| 5,227,027 A | 7/1993 | Topper | |
| 5,573,669 A | 11/1996 | Jensen | |
| 6,083,740 A | 7/2000 | Kodo et al. | |
| 6,153,665 A | 11/2000 | Goldburt et al. | |
| 6,158,169 A | 12/2000 | Goldburt et al. | |
| 6,355,172 B1 | 3/2002 | Diels et al. | |
| 6,434,881 B1 | 8/2002 | Goldburt et al. | |
| 6,476,312 B1 | 11/2002 | Barnham | |
| 6,509,188 B1 * | 1/2003 | Trosch et al. | 435/292.1 |
| 6,744,960 B2 | 6/2004 | Pelka | |
| 6,883,271 B2 | 4/2005 | Goldburt | |
| 7,008,559 B2 | 3/2006 | Chen | |
| 7,102,152 B2 | 9/2006 | Chua et al. | |
| 7,495,383 B2 | 2/2009 | Chua et al. | |
| 7,536,827 B2 | 5/2009 | Busch et al. | |

(Continued)

FOREIGN PATENT DOCUMENTS

CN    2440045 Y    7/2001

(Continued)

OTHER PUBLICATIONS

Durrett et al., "Plant triacyglycerols as feedstocks for the production of biofuels", The Plant Journal 54(4), 593-607 (2008).

(Continued)

*Primary Examiner* — Michael Marcheschi
*Assistant Examiner* — Jonathan Hurst
(74) *Attorney, Agent, or Firm* — Ella Cheong Hong Kong; Sam T. Yip

(57) ABSTRACT

The present invention relates to a multistory system for using waste carbon dioxide and waste heat to facilitate cultivation of photosynthetic organisms. In particular, the present invention relates to a multistory system with the incorporation of upconverting and downconverting luminescent materials and other components suitable for enhancing growth of photosynthetic organisms.

20 Claims, 8 Drawing Sheets

U.S. PATENT DOCUMENTS

| | | | |
|---|---|---|---|
| 7,541,537 | B2 | 6/2009 | Madigan |
| 7,662,616 | B2 | 2/2010 | Hazlebeck et al. |
| 7,682,503 | B1 | 3/2010 | Norris |
| 7,824,904 | B1 * | 11/2010 | Dimanshteyn ............. 435/292.1 |
| 7,846,391 | B2 | 12/2010 | Jaffe et al. |
| 2007/0054067 | A1 | 3/2007 | Power |
| 2007/0141695 | A1 | 6/2007 | Mitchell |
| 2008/0017875 | A1 | 1/2008 | Lee et al. |
| 2008/0216894 | A1 | 9/2008 | Hammond |
| 2008/0290319 | A1 | 11/2008 | Naum et al. |
| 2009/0004117 | A1 | 1/2009 | Rao et al. |
| 2009/0148931 | A1 | 6/2009 | Wilkerson et al. |
| 2009/0268461 | A1 | 10/2009 | Deak et al. |

FOREIGN PATENT DOCUMENTS

| | | |
|---|---|---|
| CN | 1475558 A | 2/2004 |
| CN | 1216147 C | 8/2005 |
| CN | 101045902 A | 10/2007 |
| CN | 101466824 A | 6/2009 |
| KR | 20090038313 A | 4/2009 |
| WO | WO2005/068605 | 7/2005 |
| WO | WO2006/033090 | 3/2006 |
| WO | WO2007/025145 | 3/2007 |
| WO | WO2010/132955 | 11/2010 |

OTHER PUBLICATIONS

Hu et al., "Microalgal triacylglycerols as feedstocks for biofuel production: perspectives and advances", The Plant Journal 54 (4), 621-639 (2008).

Johnson et al., "Development of an attached microalgal growth system for biofuel production ", Applied Microbiology and Biotechnology 85(3), 525-534 (2010).

Robert F. Service, "ExxonMobil Fuels Venter's Efforts to Run Vehicles on Algae-Based Oil " Science 325 (5939), 379 (2009).

Zümriye Aksu, "Biosorption of Heavy Metals by Microalgae in Batch and Continuous Systems", Wastewater Treatment with Algae, 37-35 (1998).

Brouers et al., "Immobilized cells: An appraisal of the methods and applications of cell immobilization techniques", Algal and cyanobacterial biotechnology, p. 272-293 (1989).

Darnall et al., "Selective recovery of gold and other metal ions from an algal biomass ", Environ. Sci. Technol. 20(2), 206-208 (1986).

Darnall et al., "Recovery of Heavy Metals by Immobilized Algae", Trace Metal Removal from Aqueous Solution, p. 1-24 (1986).

Khummongkol et al., "Accumulation of heavy metals in unicellular algae", Biotechnology and Bioengineering 24(12), 2643-2660 (1982).

Hameed et al., "Biotechnological Potential Uses of Immobilized Algae", International Journal of Agriculture & Biology 9(1), 183-192 (2007).

ISR for related PCT, Apr. 28, 2011, Lan Wong.

Chevalier et al., "Wastewater nutrient removal with microalgae immobilized in carrageenan", Enzyme Microb. Technol. vol. 7, p. 621-624 (1985).

Currie et al., "High-Efficiency Organic Solar Concentrators for Photovoltaics", Science, vol. 321, No. 5886, pp. 226-228 (2008).

Barnharn et al., "quantum-dot concentrator and thermodynamic model for the global redshift", Applied Physics Letters, vol. 76, No. 9, p. 1197-1199 (2000).

Rosemann et al., "Development of a cost-effective solar illumination system to bring natural light into the building core", Solar Energy, 82, p. 302-310 (2008).

Nguyen et al., "Tunable light emission using quantum dot-coated upconverters", Chem. Commun., p. 174-176, (2009).

* cited by examiner

MULTISTORY BIOREACTION SYSTEM FOR ENHANCING PHOTOSYNTHESIS

CROSS-REFERENCE TO RELATED APPLICATIONS

The present invention claims priority under 35 U.S.C. 120 to provisional U.S. Patent Application 61/413,429 filed Nov. 13, 2010 and to U.S. patent application Ser. No. 12/729,258 filed Mar. 23, 2010, the disclosures of which are incorporated herein.

TECHNICAL FIELD

The present invention relates to a multistory system for using waste carbon dioxide and waste heat to facilitate cultivation of photosynthetic organisms. In particular, the present invention relates to a multistory system with the incorporation of upconverting and downconverting luminescent materials and other components suitable for enhancing growth of photosynthetic organisms.

BACKGROUND

The greenhouse effect is mainly caused by the accumulation of excessive carbon dioxide in the earth's atmosphere. Carbon dioxide, together with water vapor, methane and other so-called greenhouse gases, absorbs infrared radiation from the sunlight and at the same time blocks the heat from escaping to space. Some heat trapped in the atmosphere is transferred to the oceans and raises their temperature as well. Global warming eventually occurs. The increase in carbon dioxide in the atmosphere is mainly due to the use of fossil fuels such as coal, oil and natural gas. The plowing of soil and deforestation also indirectly increases the content of carbon dioxide in the atmosphere.

Photosynthesis is a natural process in which living systems remove carbon dioxide from the atmosphere and transform it into organic, carbon-containing compounds. The principal photosynthetic organisms in the carbon cycle are plants, phytoplankton, marine algae and cyanobacteria. They not only play an important role in converting light energy into chemical energy in order to serve as food for higher eukaryotes in the food chain, but are important in maintaining the level of carbon dioxide in the atmosphere by consuming carbon dioxide through photosynthesis. About 100 billion metric tons of carbon per year is bound into carbon compounds by photosynthesis.

Sunlight is an essential element for the light-dependent reactions in photosynthesis. Physically, sunlight can be resolved into a vast continuous spectrum of radiation called the electromagnetic spectrum. Radiation of each particular wavelength has a characteristic amount of energy associated with it. The light spectrum which demonstrates the relative effectiveness of different wavelengths of light for a specific light-requiring process is called an action spectrum. The light-dependent reactions are mainly carried out in the range between about 380 nm and about 750 nm in the electromagnetic spectrum, that is, the visible light portion of the electromagnetic spectrum. The electromagnetic waves outside this range such as ultra-violet (UV) and infra-red (IR) do not benefit photosynthesis and are even harmful for photosynthetic organisms.

In order for light energy to be converted into chemical energy in photosynthetic organisms, it must first be absorbed by a substance called pigment. However, not all wavelengths of light can be absorbed. Most pigments in photosynthetic organisms only absorb certain wavelengths of light which are suitable for carrying out photosynthesis while other wavelengths of light will be reflected or transmitted. The light absorption pattern of a pigment is known as the absorption spectrum of that substance. When the light absorption spectrum of a pigment and the action spectrum for a specific light-requiring process are similar in pattern, such pigment is regarded as effective for this specific light-requiring process.

For example, the light absorption spectrum of chlorophyll and the action spectrum for photosynthesis are similar and therefore chlorophyll is regarded as the principal pigment for photosynthesis. In particular, chlorophyll a is essential for the oxygen-generating photosynthesis by all photosynthetic eukaryotes and in cyanobacteria; other chlorophyll subtypes such as chlorophyll b (an accessory pigment in green algae, euglenoid algae and most plants), chlorophyll c (an alternative of chlorophyll b in brown algae and diatoms), bacteriochlorophyll (in some bacteria such as purple bacteria) and chlorobium chlorophyll (in green sulfur bacteria) are chemical variants of the basic structure of chlorophyll a with slightly different absorption spectrum. Two other classes of pigments involved in capturing light energy are carotenoids and phycobilins, where the former is mainly responsible for preventing photooxidative damage to chlorophyll molecules and the later is mainly found in cyanobacteria and red algae.

In order to fully utilize the whole spectra of sunlight, upconverting luminescent (UCL) and downconverting luminescent (DCL) materials have been used in recent years to convert the non-visible light into visible light suitable for photosynthetic organisms so that they can carry out the maximum light-dependent reaction. By using these luminescent materials, photosynthetic organisms can absorb a maximum amount of light energy at a suitable wavelength.

In U.S. Pat. No. 6,883,271, a device that converts UV light into growth-enhancing light for growth of plants or vegetables is disclosed. However, such a device is limited to the conversion of UV light and is unable to convert a wide range of non-visible light into a specific wavelength of visible light for specific photosynthetic organism. It is not a self-sustained system for growing photosynthetic organisms such as algae because algae rearing require water and nutrients circulating system as well as temperature control system. In U.S. Pat. No. 7,008,559, although the use of UCL and DCL materials as light converting materials in a greenhouse setting is disclosed, its design cannot transmit the visible light efficiently from different angles to each level of a multistory building; further it is limited to the growth of herbaceous and woody plants.

In addition to removing excess carbon dioxide from the atmosphere, the above-mentioned photosynthetic organisms are candidates for alternative energy because their by-product and/or biomass can be converted into biofuel. For example, oils derived from triacylglycerols in oil seed plants (e.g. soybean, sunflower and oil palm etc.) (Durrett et al., 2008) or microalgae (Hu et al., 2008) can be made into biodiesel. Algae is more preferable as a source of biofuel since a recent study reveals that algae have inherent advantages over other sources of biofuel such as higher yield, more rapid cell division and better quality (Robert, 2009).

Therefore, there is a need in the art for an improved system for treating unwanted carbon dioxide and waste heat and efficient use of light in the cultivation of photosynthetic organisms.

SUMMARY OF THE INVENTION

The present invention relates to a multistory system for treating waste carbon dioxide and waste heat and producing photosynthetic organisms which may be used, but not exclusively in the production of biofuel. In particular, it relates to a multistory system using upconverting and downconverting luminescent materials to convert non-visible light from sunlight into visible light with wavelength suitable for the growth of photosynthetic organisms. In an exemplary embodiment, the multistory system can be self-sustaining or it can be configured for incorporation into other systems/infrastructure.

In one aspect of the present invention, the multistory system includes one or more of the following parts: (1) a carbon dioxide/waste heat receiving part; (2) a light-converting part; (3) a light collecting and distributing part; and (4) a bioreactor.

The carbon dioxide/waste heat receiving part of the present invention may include a conduit connected to one or more power plant(s) or carbon dioxide/waste heat emission source(s). The carbon dioxide/waste heat receiving part may include more than one conduits connected to any part of the multistory system where carbon dioxide and waste heat can be recycled from the multistory system back to the carbon dioxide/waste heat receiving part and further to the bioreactor. The carbon dioxide/waste heat receiving part may also include a purifying and concentrating system to extract any gas harmful for photosynthetic organisms and concentrate the carbon dioxide prior to the transfer into the bioreactor. The carbon dioxide/waste heat receiving part of the present invention may also include one or more heat pump(s). The heat pump in one embodiment is an electric closed-cycle compression heat pump capable of providing cooling and heating effects on the multistory bioreaction system of the present invention. In other embodiments, a mechanical vapor recompression heat pump can use waste heat to distill seawater to provide clean water to the bioreactors for the growth of photosynthetic organisms.

The light-converting part of the present invention may include one or more layers of downconverting and/or upconverting luminescent materials. In one embodiment, the downconverting luminescent materials used in the present invention are quantum dots which are nanoparticles selected from semiconductor, inorganic or metallic materials. Each downconverting luminescent layer may include one or more types of quantum dots. In general, quantum dots are used to absorb high-energy light including ultra-violet light and emit a narrower wavelength of lower-energy light in a range of about 300 nm to 2,000 nm. A specific wavelength of light can be selected by using different combinations of quantum dots according to the absorption spectrum of the photosynthetic pigment in a specific selected organism.

The upconverting luminescent materials in the present invention can be nanoparticles or in a bulk form and are selected from metal oxides doped with ions of lanthanides or transition metal compounds. Upconverting luminescent materials in nanoparticles form are more preferable in the present invention because they are lower in light scattering and higher in luminescent efficiency than the same materials in bulk form. In general, upconverting luminescent materials are used to absorb infra-red light or near infra-red light and emit a shorter wavelength of higher-energy visible light in a range of about 400 nm to 800 nm. In combination with the quantum dot layer(s) of the present invention, the upconverted emission from the upconverting luminescent layer of the present invention may be partly or wholly absorbed by the quantum dot layer(s) and a desirable wavelength of light re-emitted. The layers of upconverting and downconverting luminescent materials may also be covered by one or more transparent layer(s). These materials form at least a portion of the roof, at least one surface of the bioreactor of the present invention and optionally a portion of the sidewalls of the multistory system.

The multistory system of the present invention may also include a solar lighting device which comprises a light pipe and/or one or more heliostat(s). The light pipe may further include one or more of the following components: prismatic light guides, lens guides, reflective metal tubes, mirror ducts, fiber optics or other light transport devices. The light pipe may be situated inside the multistory system or separated from the multistory system. In an exemplary embodiment, a heliostat is situated at each floor outside the multistory system. The heliostat may further include one or more emitters and/or diffusers. The light pipe or the heliostat may additionally be coated with one or more layers of upconverting and/or downconverting luminescent materials. Additional reflective elements such as glasses or mirrors may be used to direct light from the emitters or diffusers to the bioreactor of the present invention. The light-converting part may further include one or more photovoltaic device(s) which comprises one or more of the quantum dot layer(s). Energy from the photovoltaic devices can be used to power water pumps, air circulators, etc., to make the multistory plant self-sufficient.

In the bioreactor of the present invention, photosynthetic organisms are grown. Photosynthetic organisms may include oil seed plants and algae. The photosynthetic organisms of the present invention can be naturally-occurring or genetically-modified organisms which are capable of carrying out photosynthesis. These organisms may be used in the production of biofuel and other by-products. Algae are cultivated in an exemplary embodiment of the present invention. The bioreactor of the present invention optionally includes one or more water bath(s) to control the temperature in the bioreactor. The bioreactor of the present invention may additionally include a nutrients supply. At least one surface of the bioreactor of the present invention may also be coated with one or more layers of the upconverting and downconverting luminescent materials.

Another aspect of the present invention is to provide methods of using waste carbon dioxide and waste heat for cultivating photosynthetic organisms. The method of treating the waste carbon dioxide/waste heat of the present invention may include the following steps: collecting carbon dioxide/waste heat from a power plant, manufacturing facility, or other source of waste carbon dioxide/waste heat and/or recycling carbon dioxide from a multistory system with bioreactors, transferring carbon dioxide to bioreactors, supplying photosynthetic organisms and nutrients to the bioreactors, converting non-visible light into visible light and transmitting thereof to the bioreactors for the growth of photosynthetic organisms, and collecting the photosynthetic organisms into one or more processor(s) for harvesting and refining. The processor(s) may be situated inside the multistory system or separated from the multistory system.

The present invention is applicable to a high carbon dioxide emission/waste heat site such as a power plant or other high carbon dioxide-emitting manufacturing facility. Furthermore, use of the photosynthetic organisms produced in the present invention may optionally be used for the production of biofuel.

BRIEF DESCRIPTION OF THE DRAWINGS

These and other objects, aspects and embodiments of this claimed invention will be described hereinafter in more details with reference to the following drawings, in which:

DETAILED DESCRIPTION

Figure 1:
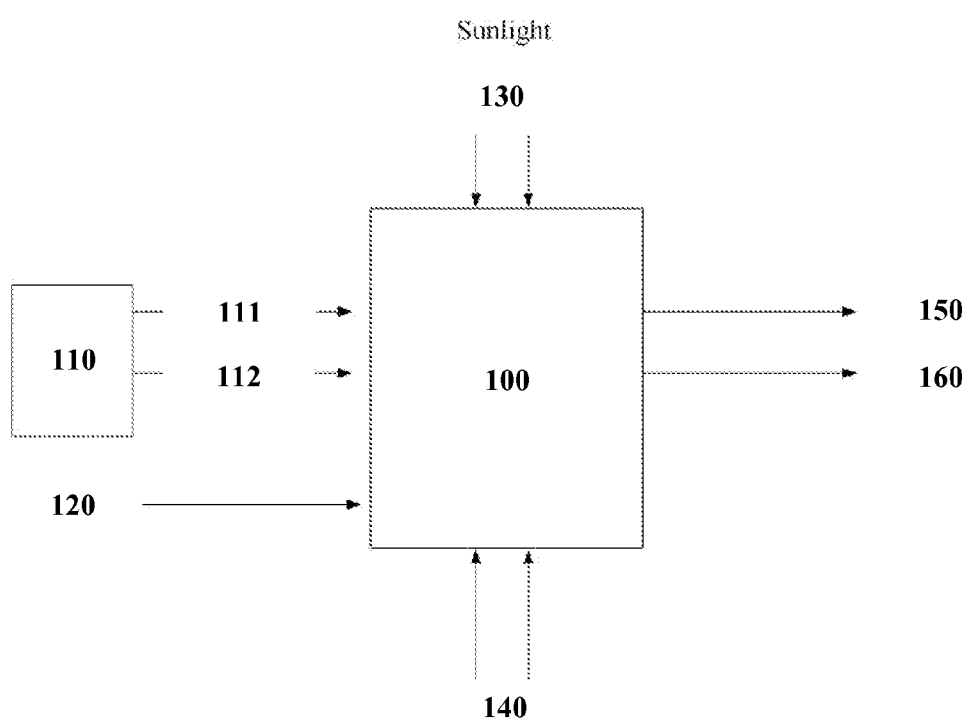
FIG. 1 is a flow chart depicting a multi-story building equipped with the system of the present invention for the culture of photosynthetic organisms and its interactions with other necessary components.

FIG. 1 is a schematic diagram depicting the interactions between a multistory bioreaction system 100 and other components which are used for the photosynthetic organisms in the system to carry out light-dependent reaction of photosynthesis and to produce biofuel and other by-products. The multistory system 100 receives waste carbon dioxide 111 and waste heat 112 from the power plant 110. Other sources (not shown in the figure) can also be used to supply carbon dioxide and/or waste heat. The multistory system 100 also receives seawater from the sea 120 or other source (not shown in the figure) for the operation of water bath (not shown in the figure) and bioreactor (not shown in the figure) in the multistory system 100. The seawater source can be replaced by freshwater source subject to the photosynthetic organism to be grown in the bioreactor. In either the seawater source or freshwater source, photosynthetic organisms may also be obtained for the system to be grown in the bioreactor. Alternatively, the photosynthetic organisms may be obtained from other sources. Multistory system 100 also requires sunlight 130 or light from an artificial source (not shown in the figure) with or without the whole spectra of electromagnetic radiation. For example, the light source can include UV light, IR or any kind of radiation in the wavelengths which are available in the whole spectra of electromagnetic radiation. Multistory system 100 further includes a series of light-converting and light-transmitting devices (not shown in the figure) for converting light from the light source into a specific wavelength or narrower range of wavelengths of light and directing the converted light to the bioreactor in the system. The bioreactor itself is also coated with the light-converting device to convert incident light into suitable wavelength for the photosynthesis of the microorganisms therein. In addition, photovoltaic devices (not shown in the figure) are also incorporated to convert the light energy from the light source into electrical energy for the system or for other operations.

Multistory system 100 also requires a nutrient source 140. The nutrient source 140 may supply nitrogen, phosphate, potassium, zinc and any other essential elements for the photosynthetic organisms to carry out photosynthesis. It can be obtained from any waste plants (not shown in the figure) or by recycling from the by-products of a biofuel plant (not shown) which may be located off-site. Photosynthetic organisms housed in each of the bioreactors generate oxygen 150. The biofuel 160 generated directly from photosynthesis or the biomass of the photosynthetic organisms which contains biofuel 160 is sent to one or more processor(s) or plant(s) for further processing to biofuel and/or other by-products. Optionally, the processor(s) may be included in the multistory system or may take place in a separate facility.

In the multistory system 100, the light-converting device is a series of luminescent materials which can either up-convert the lower-energy light or down-convert the higher-energy light into a spectrum of or a specific wavelength of light absorbable by the pigment of the photosynthetic organisms for conducting photosynthesis. These materials are situated on the roof of the multistory system, on the surface of the bioreactor and, optionally, at least a portion of the walls. In order to achieve light converting, different types of upconverting and downconverting luminescent materials are used.

Figure 2A:
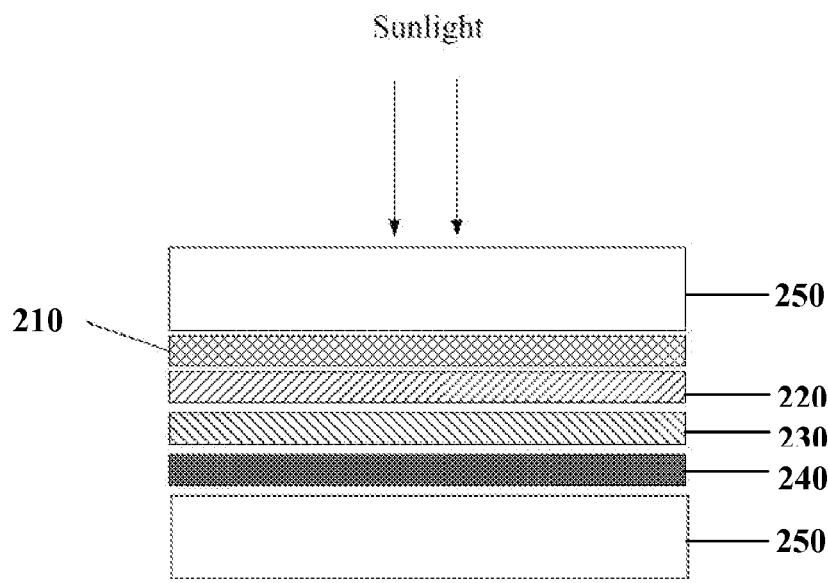
FIG. 2a schematically represents a combination of an upconverting luminescent layer and quantum dot layers in the light-converting system of the present invention.

In FIG. 2a, a layer of upconverting luminescent material 210 is situated above three layers of three different kinds of quantum dots 220, 230, 240 to form a sandwich of luminescent material layers. A first quantum dot layer 220 is composed of a plurality of first quantum dot nanoparticles. A second quantum dot layer 230 is composed of a plurality of second quantum dot nanoparticles. A third quantum dot layer 240 is composed of a plurality of third quantum dot nanoparticles. Different types of quantum dot nanoparticles can be distinguished by a difference in materials, a difference in particle size or a difference in size distribution. In other words, it is possible that three different layers of quantum dot nanoparticles are made of the same material but have different particle sizes or size distributions. For example, the first quantum dot layer may be composed of CdSe quantum dot nanoparticles of 5.0 nm in diameter to emit radiation having a center wavelength of about 625 nm while the second quantum dot layer is composed of CdSe quantum dot nanoparticles of 2.2 nm in diameter to emit radiation having a center wavelength of about 500 nm.

Figure 2B:
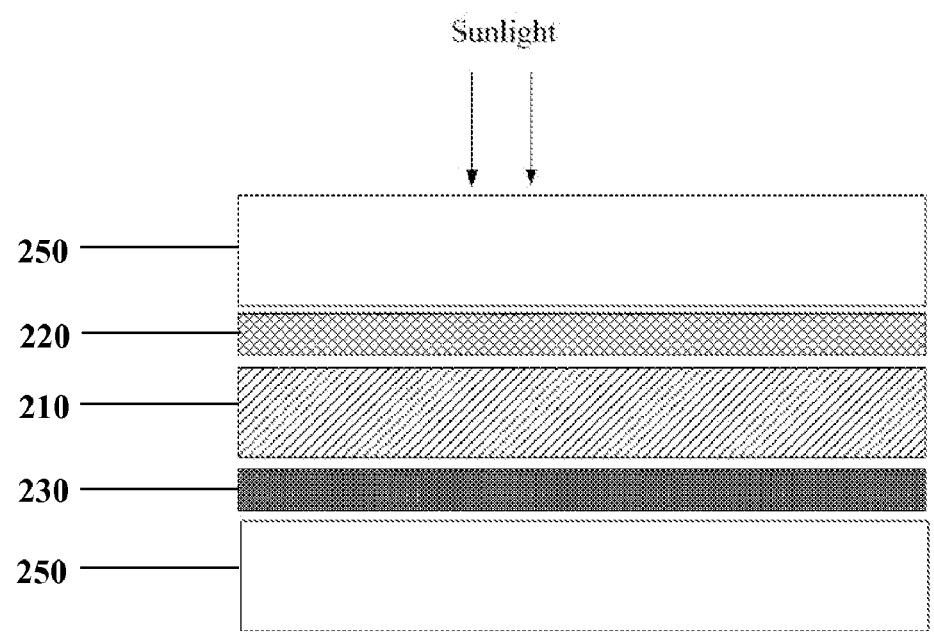
FIG. 2b schematically represents a combination of an upconverting luminescent layer being sandwiched between two quantum dot layers.

In FIG. 2b, the upconverting luminescent layer 210 is sandwiched between a first quantum dot layer 220 and a second quantum dot layer 230. The use of different combinations and sequences of quantum dot layers and upconverting layer(s) result in different conversion profiles. The upconverting and downconverting luminescent layers are further covered by a glassy layer 250, which can be substituted by polymeric materials or any transparent materials, on top and bottom of the sandwich, to protect the upconverting and downconverting layers.

Microscopically, each quantum dot nanoparticle optionally includes a core and a cap. The core is mainly made of semiconductor selected from IIA-VIA, IIIA-VA, IVA-IVA and IVA-VIA semiconductor. The size of the core ranges from about 1 nm to 50 nm, preferably about 1 nm to 25 nm, more preferably about 1 nm to 10 nm, and most preferably about 1 nm to 5 nm. The size of the cap ranges from about 0.1 nm to 10 nm, more preferably about 0.1 nm to 5 nm, and most preferably about 0.1 nm to 2 nm. The cap passivates the core by providing a wide band gap. The material of the cap is also different from that of the core in order to form a potential barrier around the core. For example, the cap may be made of CdS while the core may be made of CdSe.

Upconverting luminescent materials are typically selected from metal oxides doped with ions of lanthanides such as $Er^{3+}$, $Tm^{3+}$ and $Yb^{3+}$. However, other materials such as transition metal compounds, e.g. $Yb^{3+}$ doped with $CsMnCl_3$ may also be used. The upconverting luminescent material can be in nanoparticle form or in bulk form. As compared to the bulk form, the nanoparticulate upconverting luminescent material has lower light scattering and higher luminescent efficiency.

Figure 3:
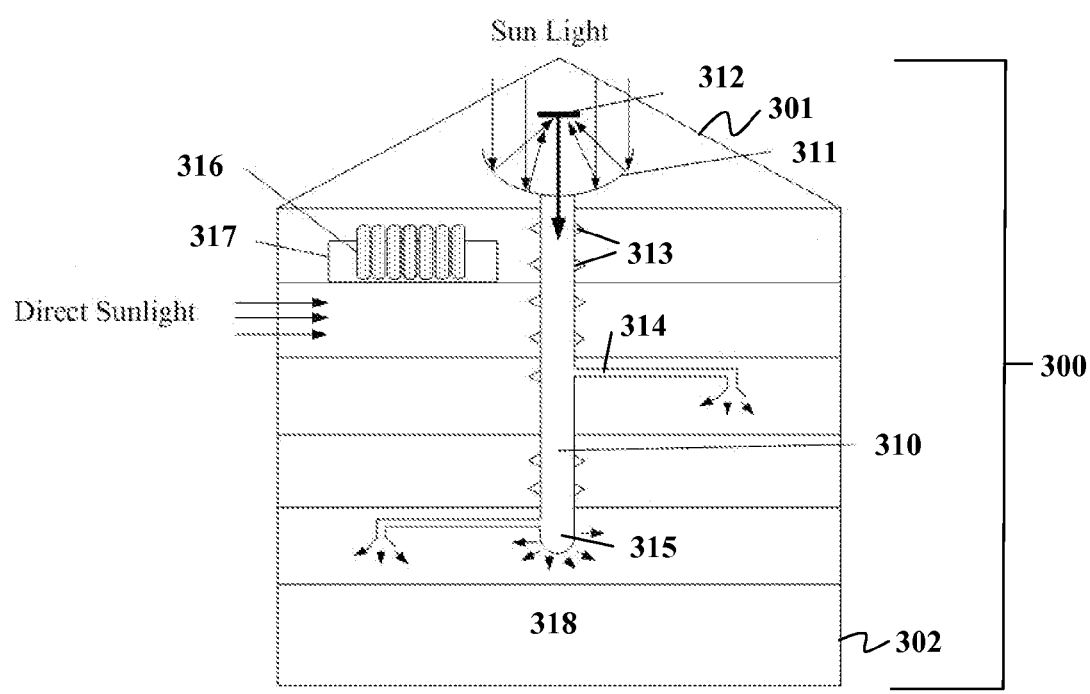
FIG. 3 schematically represents a cross-sectional view of a multistory system.

FIG. 3 is a cross-sectional view of the multistory system 300. A light pipe 310 is situated along the central axis of the system protruding towards the rooftop where the sunlight can reach and extending to lower levels where bioreactors 316 are situated. The roof top 301 and optionally at least a portion of the walls of the multistory system are covered by light-converting materials including but not limited to upconverting and/or downconverting luminescent materials in a structure such as that depicted in FIG. 2. Close to the roof top, the light pipe comprises a primary optical element 311 and a second optical element 312. The primary optical element 311 can be a mirror with concave surface or a converging mirror to collect the sunlight and then reflect to the second optical element 312. The secondary optical element 312 can be an optical mirror or reflector. Preferably, the secondary optical element is also capable of absorbing at least some of heat from the focused light and redirecting towards the light pipe. The primary or secondary optical element optionally further comprises one or more photovoltaic cells (not shown in the figure) to convert the sunlight into electricity to operate equipment(s) such as water pumps for the bioreactors.

The light pipe 310 can be in a form of one or more prism light guides (not shown in the figure). These prism light guides are hollow tubes with a rectangular or circular cross-section having bounding surfaces made of thin prisms. The prismatic portions of the prism light guides are situated outside the main conducting tube of the light pipe; whereas the interior surfaces thereof are smooth and flat. The interior surfaces of the prism light guide can be lined with highly reflective multilayer dielectric films. Light rays propagating down the hollow tube strike the smooth surface and are partially reflected and refracted. The reflected rays continue down along the main conducting tube of the light pipe; whereas the refracted rays pass a short distance to the prismatic edges where they are totally internally reflected and then emerge again into the hollow interior surfaces of the prism light guide.

At each level of the multistory system, the light pipe 310 further comprises an aperture and/or emitter 313. Aperture and/or emitter 313 are used to remove the light at various heights through the multistory building. The aperture and/or emitter can be replaced by a dispersing system 314 having an extended duct connected to the main conducting tube of the light pipe. The dispersing system 314 is used to transmit some light to the area remotely from the main conducting tube of the light pipe. At the end of the main conducting tube of the light pipe, a diffuser 315 is included to diffuse the light and provide a uniform illumination to the last level which includes bioreactors of the multistory building (since one or more lower levels, e.g., ground level or underground level, are used to house various types of equipments such as pumps, centrifuges or ultrasound or filtration system for harvesting photosynthetic organisms, settling ponds for flocculation with or without flotation, etc). The diffuser 315 may be a convex lens or any expanding lens. The diffuser 315 functions in a similar manner to the dispersing system 314 but differs in the effective part of the system. If desired, the aperture/emitter/diffuser/dispersing device or any part of the light pipe can be covered with the light-converting device set forth in the present invention.

At each level of the multistory system 300, a cluster of bioreactors 316 are located. To maintain the bioreactors at a temperature suitable for growth of photosynthetic organisms, bioreactors 316 are optionally surrounded by water bath 317.

In each of the bioreactors 316, photosynthetic organisms are kept and grown in the presence of necessary nutrients and carbon dioxide. One or more layers of the upconverting and downconverting luminescent materials are also coated on the bioreactor 316. The particular photosynthetic organism may be selected from cyanobacteria (Cyanophyceae), green algae (Chlorophyceae), diatoms (Bacillariophyceae), yellow-green algae (Xanthophyceae), golden algae (Chrysophyceae), red algae (Rhodophyceae), brown algae (Phaeophyceae), dinoflagellates (Dinophyceae) or 'pico-plankton' (Prasinophyceae and Eustigmatophyceae) or any other photosynthetic material which can be grown in the environment of current invention and may be used for creating fuel or food or a combination of both.

Carbon dioxide is supplied from a carbon dioxide emission source (not shown in the figure) such as a power plant or an incineration plant, or is circulated from the multistory system itself, to each of the bioreactors, typically by introduction through a gas diffuser into the liquid of the bioreactor. However, depending upon the selected photosynthetic organism, absorption of carbon dioxide from the atmosphere within the multistory structure may be sufficient. The medium in the water bath 317 optionally used to control the temperature of the bioreactor 316 may be seawater, freshwater or water circulated from other parts of the system. Water bath 317 can be separated from the bioreactors 316.

Further down to the ground floor 302 (and optionally one or more below-ground levels) of the multistory system, a processing system 318 is incorporated into the system to control the input and output of the substances. The processing system 318 also controls the circulation of the substances within the system using one or more pumps. Further, settling pond(s) for flocculation, centrifuge(s) or ultrasound or filtration system for harvesting photosynthetic organisms, device(s) for dewatering or drying the biomass of the photosynthetic organisms, and systems for oil extraction and conversion etc. may be included on this/these floor(s). In addition, the processing system 318 may also have an electricity storage device (not shown in the figure) to store the unused electrical energy generated from the photovoltaic device of the system. Optionally, the exterior walls of the ground floor are covered with opaque, heat-resistant materials since the bioreactors are not located at this level.

Figure 4:
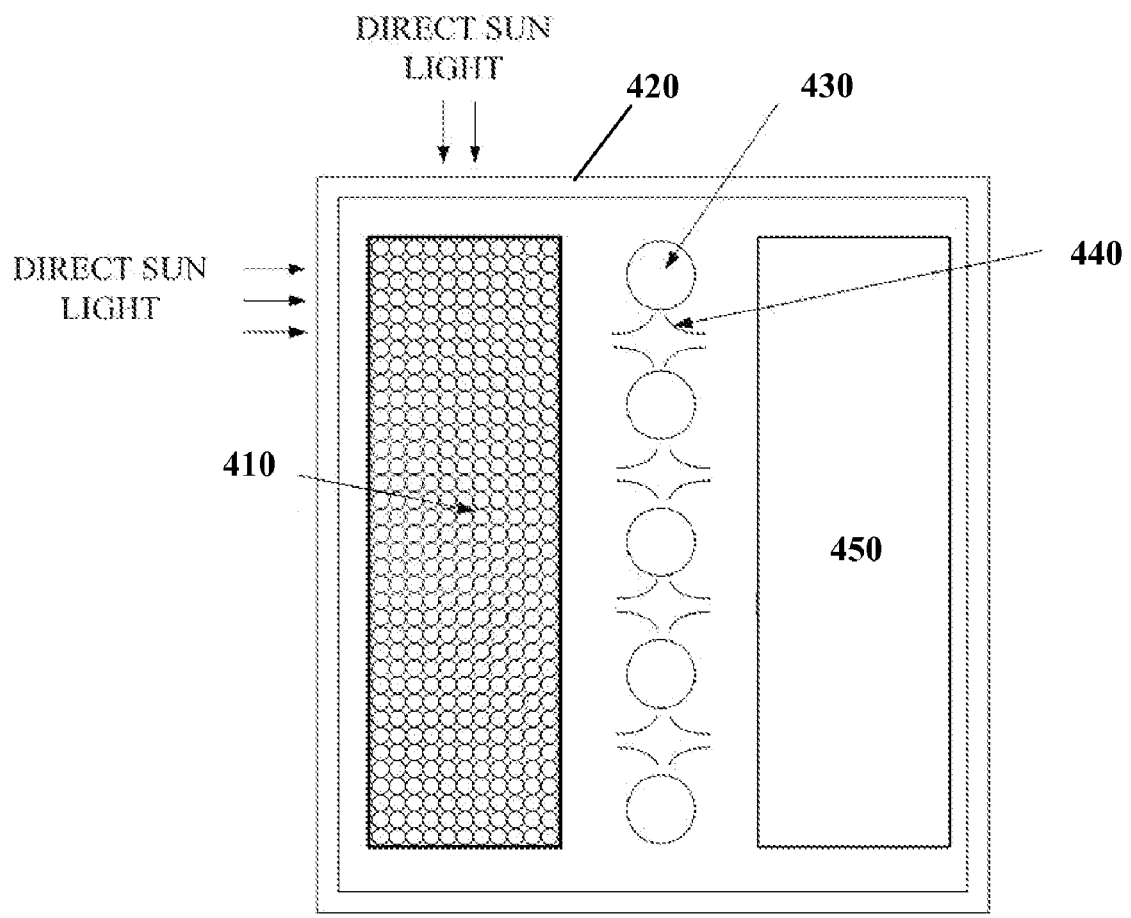
FIG. 4 schematically represents a transverse view of one level of the multistory system.

FIG. 4 is a cross-section of one level of the multistory system. Bioreactor-containing water bath 410 receives light directly through the cover 420 of the multistory system or from the light pipe 430. The cover 420 is coated with the light-converting material of FIG. 2 and is transparent or translucent. Reflective mirrors or lens 440 are positioned next to the opening of the light pipe to direct the light from the aperture (not shown in the figure) of the light pipe 430 to the direction for which the bioreactor receives maximum light intensity. Water bath 450 may be separated from the bioreactors to serve as a general temperature control system for other parts of the multistory system.

Figure 5:
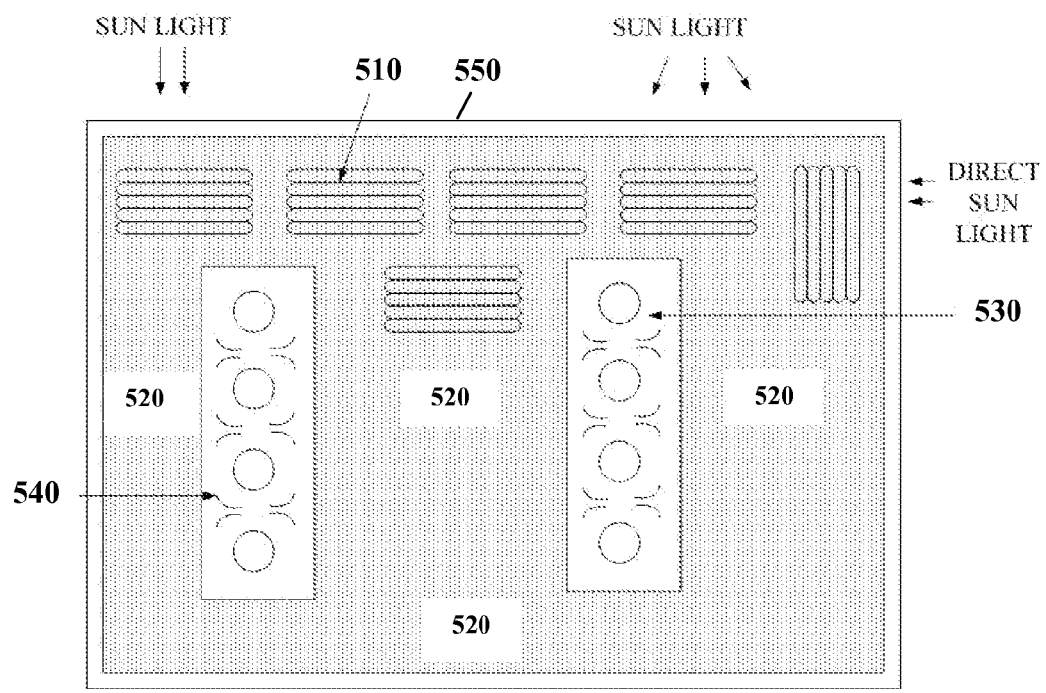
FIG. 5 schematically represents a transverse view of another level of the multistory system.

FIG. 5 is a cross-section of another level of the multistory system. At this level, the water bath 520 occupies most of the floor plan surrounding a plurality of bioreactors 510 having an elongated cross-section in this example. At the outlet of the light pipe 530, there is a plurality of reflective mirrors or lenses 540 to direct the light to the bioreactor. The elongated bioreactors 510 are aligned in parallel such that the elongated side of each bioreactor is perpendicular to the sunlight directed through the cover 550 of the multistory system. This is because the larger the surface of the bioreactor that faces the light, the greater the light intensity that will be absorbed by the photosynthetic organism. The cover 550 is coated with the light-converting materials of FIG. 2 and is transparent or translucent. The heat transmitted from an external source such as a power plant (not shown in the figure), generated from the photovoltaic cell (not shown in the figure), or recycled from any part of the multistory system, can be used to increase the temperature of the water bath. For algal growth, the temperature in the water bath is preferably kept between 10° C. and 35° C. and the optimal temperature is subject to the species of the algae in the bioreactors.

Figure 6:
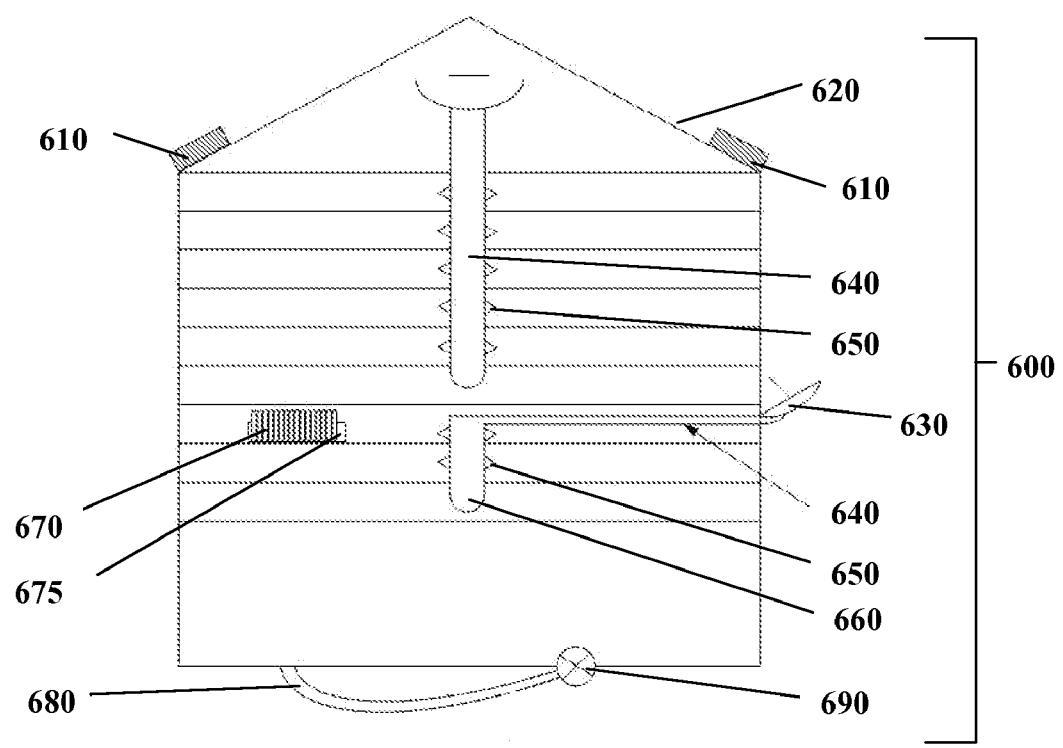
FIG. 6 schematically represents a situation in which some self-sustained components and heliostats are incorporated into the multistory system.

In FIG. 6, photovoltaic cells 610 are positioned at the edges of the roof top of the multistory system 600 where the cells are optionally covered by a light-converting device 620 to enhance the electrical output of the photovoltaic cells. The photovoltaic cells 610 mainly function to absorb the sunlight and convert it to electricity by using the electric current generated upon the interaction of absorbed light with the components of the active layer of the cell. The active layer (not shown in the figure) of the photovoltaic cell 610 is selected from organic materials, inorganic materials or a combination of both. Light-converting device 620 can assist in the photovoltaic current efficiency by using a quantum dot layer in a waveguide as concentrators for photovoltaic cells and to redshift the light entering the photovoltaic device. Furthermore, photovoltaic cells can optionally be positioned over the walls (for example, the junction of walls) to meet the electrical needs of the system.

The multistory system 600 further comprises one or more heliostats 630 to track, collect and collimate the sunlight to a light distribution system 640 and then further transmit the light to the desired bioreactor. Heliostat 630 can be a single tracking mirror or a combination of a concave tracking mirror with a secondary flat mirror. Both function to direct the sunlight from the side of a multistory building into one or more lower floors of the system. Along or at the end of the light distribution system, emitter 650 and/or diffuser 660 may be present to remove various light through the system and provide uniform illumination respectively to the bioreactor 670. If desired, the emitter or diffuser can be covered with the light-converting material of FIG. 2 of the present invention. Heliostats can be used for multistory buildings having a height of greater than 30 meters (greater than approximately 10 stories).

At the ground level of the multistory system, an underground water pipe 680 and a water temperature adjustment device 690 are connected together with the processing system. The underground water pipe 680 is configured to run through the underground so as to cool down the circulating water from the water bath 675 or the bioreactor 670. This is typically used during summer months or in warm climate areas. A waste heat recovery boiling device is integrated as part of a water temperature adjustment device 690 into the multistory system to heat the seawater or freshwater from a water source (not shown in the figure) may be used in colder climates during winter months. Alternatively, a heat pump, typically an electric closed-cycle compression heat pump using waste heat as a heat source, which provides both cooling and heating to the multistory system is installed as a water temperature adjustment device 690. Other possible systems which assist the treatment of carbon dioxide (e.g., removal of toxic fumes from power plant effluent) and the production of biofuel can optionally be incorporated into the multistory system 600.

Figure 7:
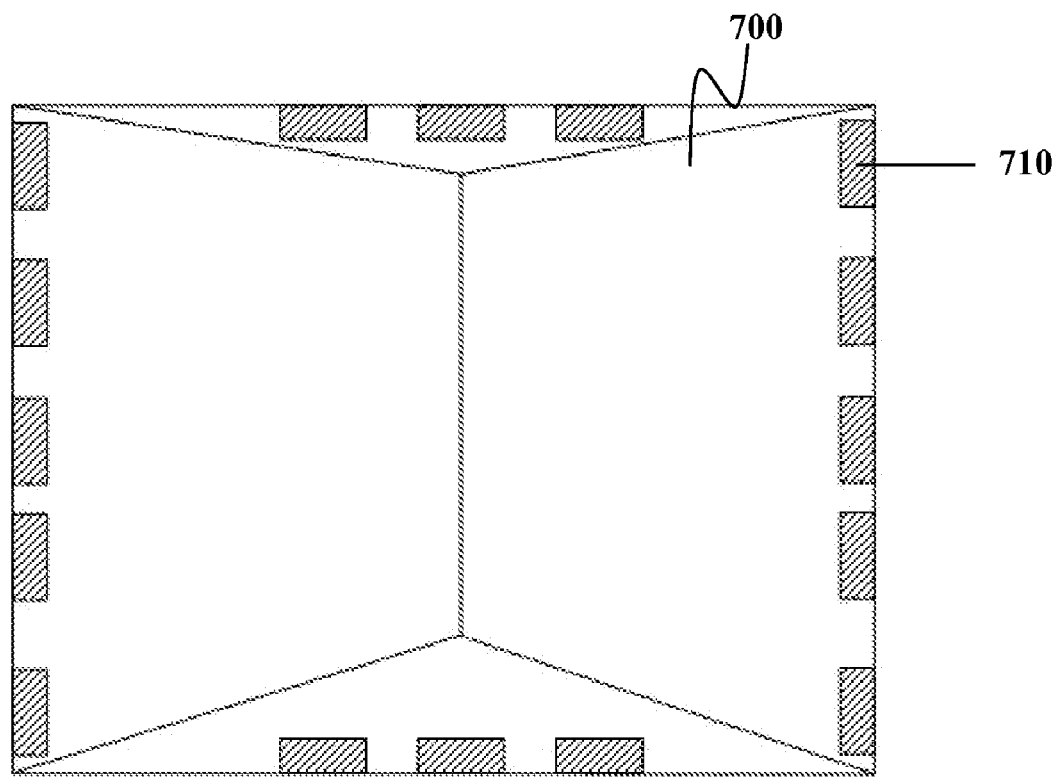
FIG. 7 schematically represents a top view of the roof of a multi-level building equipped with the system of the present invention.

FIG. 7 shows a top view of the multistory system in the example of FIG. 6. From the top view, the photovoltaic cells 710 (with optional light-converting covers) are positioned over the edges of the roof top of the multistory system 700. The number of photovoltaic cells is subject to the needs of the system, mainly the electrical. As described in the above embodiments, the roof top of the multistory system is covered with the light-converting device set forth in FIG. 2 of the present invention. The position of the photovoltaic cells 710 in this embodiment is to avoid shadowing the sunlight directed to the light-converting device covered on the surface of the roof top.

Figure 8:
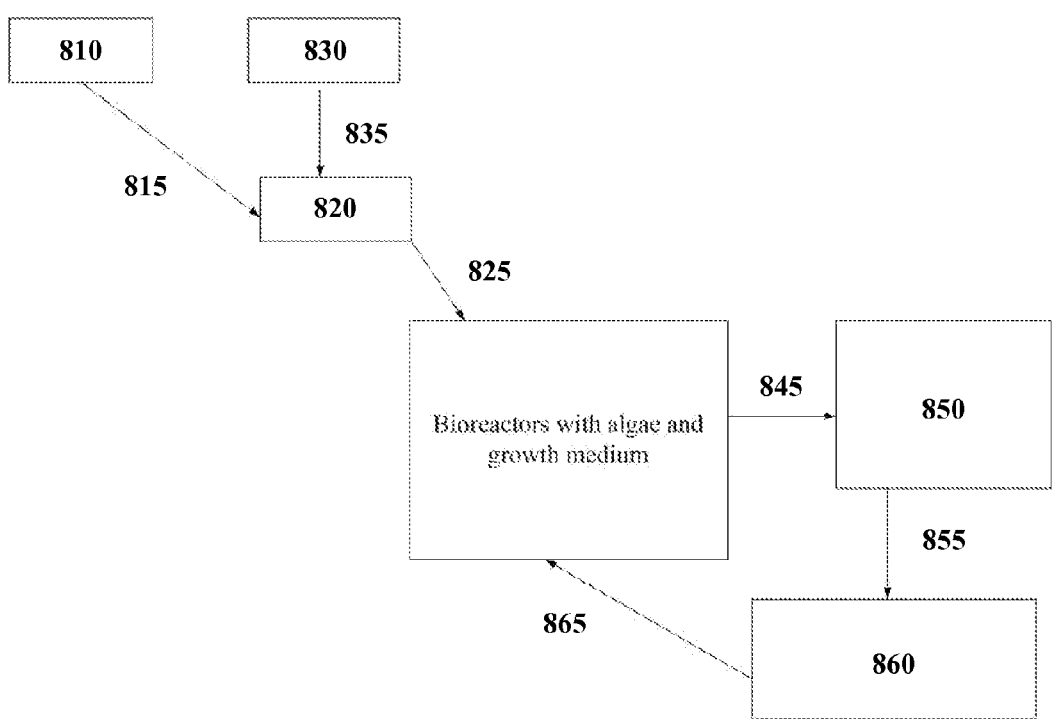
FIG. 8 is a flow chart depicting a self-sustaining model of the multistory system.

FIG. 8 is a flow chart showing the flow of substance(s) from different parts of the multistory system. Power plant 810 is one of the sources of waste carbon dioxide and waste heat 815. Carbon dioxide is introduced into the liquid of the bioreactor for the growth of photosynthetic organism and waste heat is transferred to one or more heat pump(s) 820. Photovoltaic cells 830 absorb sunlight or red-shifted light from the quantum dot layer of the light-converting device (not shown in the figure) to generate electricity 835 and supply the heat pump(s) 820. The majority of the heat pumps in the technical field work on the principle of the vapor compression cycle. In one example of these heat pumps, the waste heat is extracted from the heat emission source (i.e. waste heat 815 in current model) to boil a circulating substance within the pump. Then a compressor (not shown in the figure) compresses the circulating substance and raises its pressure and temperature to a level where its energy becomes available for use. The heat is delivered to the condenser and then pumped to the reboiler (not shown in the figure). The work of the compressor requires external input of electricity, preferably the electricity needed can be provided by the photovoltaic cells 830 in the multistory system. A mechanical vapor recompression heat pump system 820 can distill water from the sea in order to supply clean water 825 to the bioreactor and/or water bath (not shown in this figure) as the high energy requirements of distillation can typically be reduced by using a heat pump system. Optionally another heat pump device 820 using waste heat as a heat source can provide both cooling and heating effects on the multistory system. Electric closed-cycle compression heat pumps are typically installed, but a few absorption heat pumps and heat transformers can also be used for water heating and cooling. The by-product of photosynthesis and the biomass of the photosynthetic organism 845 from the bioreactor are harvested, collected and processed in one or more processor(s) 850. The remaining cells and the waste water 855 are transferred to a circulating system 860 where UV is one of the means to sterilize the waste water and cells 855. The circulating system 860 will supply the sterilized water and cells 865 into the bioreactor as part of substance input for another growth cycle of photosynthetic organisms. This flow chart demonstrates that the multistory system is highly self-sustained and fully utilizes the waste carbon dioxide, natural light source and waste heat to become chemical energy (harvested photosynthetic organisms).

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

What is claimed is:

1. A multistory bioreaction system comprising:
    a roof incorporating a light-converting material including one or more layers of upconverting luminescent materials and one or more layers of downconverting luminescent materials, the upconverting and the downconverting luminescent materials being selected to convert incident light into light suitable for photosynthetic organisms;
    sidewalls supporting the roof that at least partially incorporate the light-converting material including one or more layers of upconverting luminescent materials and one or more layers of downconverting luminescent materials;
    a light pipe having a collector positioned adjacent to the roof for collecting sunlight and transmitting the light to multiple stories of the multistory bioreaction system via light conduits positioned within the multistory bioreaction system;
    a plurality of bioreactors for housing photosynthetic organisms in a nutrient-including medium and positioned to receive light from the light pipe and light conduits to conduct photosynthesis;
    a conduit positioned to communicate between a waste carbon dioxide emitting source and waste heat emitting source and the interior of the multistory bioreaction system to supply carbon dioxide and heat to the bioreactors;
    wherein the one or more layers of downconverting luminescent materials comprise particles including one or more semiconductors selected from IIA-VIA, IIIA-VA, IVA-IVA or IVA-VIA materials.

2. The multistory bioreaction system of claim 1 wherein the photosynthetic organisms are algae.

3. The multistory bioreaction system of claim 1 further comprising one or more water baths surrounding one or more bioreactors for maintaining the bioreactors at a selected temperature or range of temperatures.

4. The multistory bioreaction system of claim 1 further comprising one or more heliostats positioned on one or more sides of the multistory bioreaction system for collecting sunlight via a heliostat light collector and transmitting the sunlight from the heliostat light collector to lower floors of the multistory bioreaction system via optical conduits.

5. The multistory bioreaction system of claim 4 wherein the heliostat light collector is covered with a light-converting material including one or more layers of upconverting luminescent materials and one or more layers of downconverting luminescent materials.

6. The multistory bioreaction system of claim 1 wherein the collector of the light pipe is covered with a light-converting material including one or more layers of upconverting luminescent materials and one or more layers of downconverting luminescent materials.

7. The multistory bioreaction system of claim 1 wherein each of said plurality of bioreactors is covered with a light-converting material including one or more layers of upconverting luminescent materials and one or more layers of downconverting luminescent materials.

8. The multistory bioreaction system of claim 1 further comprising a plurality of photovoltaic cells positioned along edges of the roof and/or walls such that the photovoltaic devices do not interfere with the sunlight transmitted into the multistory bioreaction system.

9. The multistory bioreaction system according to claim 1, wherein the downconverting converting luminescent material of said light-converting device comprises a quantum dot.

10. The multistory bioreaction system according to claim 9, wherein a core of the quantum dot comprises one or more materials selected from IIA-VIA, IIIA-VA, IVA-IVA and IVA-VIA semiconductors.

11. The multistory bioreaction system according to claim 10, wherein the size of the core of said quantum dot is in a range of 1 nm to 50 nm.

12. The multistory bioreaction system according to claim 3 further comprising one or more heat pumps for using the waste heat for maintaining the one or more water baths at a selected temperature or range of temperatures.

13. The multistory bioreaction system according to claim 1 further comprising one or more heat pumps for using the waste heat to distill seawater or waste water to provide clean water to the bioreactors for the growth of the photosynthetic organisms.

14. A method of enhancing the cultivation of photosynthetic organisms comprising:
    providing a multistory bioreaction system according to the system of claim 1;
    receiving light through the upconverting and downconverting luminescent materials such that the wavelength range of the received light is substantially in a range useful for photosynthesis;
    housing photosynthetic organisms in one or more bioreactors positioned within the multistory bioreaction system and receiving light through the upconverting and downconverting luminescent materials; and
    supplying waste heat and waste carbon dioxide from an external source to the photosynthetic organisms to enhance photosynthesis.

15. A method of enhancing the cultivation of photosynthetic organisms according to claim 14 wherein the photosynthetic organisms are precursor organisms for the production of biofuel.

16. A method of enhancing the cultivation of photosynthetic organisms according to claim 15 wherein the photosynthetic organisms are algae.

17. A method of enhancing the cultivation of photosynthetic organisms according to claim 14 wherein the bioreactors further house water and nutrients for the photosynthetic organisms.

18. A method of enhancing the cultivation of photosynthetic organisms according to claim 17 further comprising circulating the water and nutrients by pumping wherein photovoltaic cells provide at least a portion of energy required for pumping the water and nutrients.

19. A method of enhancing the cultivation of photosynthetic organisms according to claim 14 further comprising providing light from an uppermost surface of the multistory bioreaction system to lower stories of the multistory bioreaction system via a light pipe.

20. A method of enhancing the cultivation of photosynthetic organisms according to claim 16 further comprising harvesting the algae by methods including centrifugation, flocculation, filtration or ultrasound wave.

* * * * *